United States Patent [19]

Diaz

[11] Patent Number: 4,855,522
[45] Date of Patent: Aug. 8, 1989

[54] PRODUCTION OF AROMATIC HYDROCARBONS

[75] Inventor: Henri Diaz, Martigues, France

[73] Assignee: The British Petroleum Company p.l.c., London, England

[21] Appl. No.: 168,701

[22] Filed: Mar. 16, 1988

[30] Foreign Application Priority Data

Mar. 19, 1987 [GB] United Kingdom ............... 8706503

[51] Int. Cl.$^4$ ............................................ C07C 12/02
[52] U.S. Cl. ........................ 585/417; 585/415; 585/418
[58] Field of Search ................... 585/415, 417, 418

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 4,120,910 | 10/1978 | Chu | 260/673 |
| 4,157,293 | 6/1979 | Plank et al. | 208/135 |
| 4,180,689 | 12/1979 | Davies et al. | 585/407 |
| 4,350,835 | 9/1982 | Chester et al. | 585/415 |
| 4,417,083 | 11/1983 | Bernard et al. | 585/419 |
| 4,490,569 | 12/1984 | Chu et al. | 585/415 |
| 4,543,347 | 9/1985 | Heyward et al. | 502/61 |
| 4,565,897 | 1/1986 | Gane et al. | 585/415 |
| 4,613,716 | 9/1986 | McNiff | 585/415 |
| 4,642,403 | 2/1987 | Hyde et al. | 585/415 |
| 4,654,316 | 3/1987 | Barri et al. | 502/61 |
| 4,654,454 | 3/1987 | Barri et al. | 585/415 |

FOREIGN PATENT DOCUMENTS

| | | |
|---|---|---|
| 0002899 | 7/1979 | European Pat. Off. . |
| 0002900 | 7/1979 | European Pat. Off. . |
| 0024930 | 3/1981 | European Pat. Off. . |
| 0050021 | 4/1982 | European Pat. Off. . |
| 1507778 | 4/1978 | United Kingdom . |

*Primary Examiner*—Curtis R. Davis
*Attorney, Agent, or Firm*—Larry W. Evans; Joseph G. Curatolo; Sue E. Phillips

[57] ABSTRACT

A process for producing aromatic hydrocarbons comprising bringing into contact a hydrocarbon feedstock containing a $C_2$, $C_3$ and/or $C_4$ paraffinic hydrocarbon with a catalyst composition comprising an aluminosilicate in which the molar ratio of silica to alumina is at least 5:1 and loaded with a compound of (a) gallium and (b) at least one rear earth metal.

12 Claims, No Drawings

PRODUCTION OF AROMATIC HYDROCARBONS

The present invention relates to a process for producing aromatic hydrocarbons from a hydrocarbon feedstock comprising $C_2$, $C_3$ and/or $C_4$ hydrocarbons over a novel catalyst system.

Hitherto synthetic routes to producing aromatics from open chain hydrocarbons have started either from feedstocks which have at least three carbon atoms or from feedstocks which contain $C_2$ hydrocarbons as the major component. Feedstocks containing 3 or more carbon atoms are initially dimerised and the dimerised product is subsequently cyclised over a variety of catalysts e.g. over a gallium/zeolite system at elevated temperatures. Such processes are described for example in our British Pat. Nos. 1507778 and 1561590. On the other hand hydrocarbon feedstocks which have a major $C_2$ component have been converted to aromatics at temperatures above 580° C. as claimed and described in our published European Patent Application No. 0050021. Aromatic hydrocarbons produced in this manner are usually accompanied by small quantities of open chain hydrocarbons and together are useful amongst others as gasoline blending components.

It has now been found that the presence of a rare earth metal compound in the catalyst composition can have a significant beneficial effect, for example on the selectivity to aromatics obtained on reaction of $C_2/C_3/C_4$ hydrocarbons at temperatures below that required for aromatisation of these hydrocarbons when using gallium/zeolite systems alone, or in a reduced level of carbon deposited on the catalyst during the process.

Accordingly, the present invention is a process for producing aromatic hydrocarbons comprising bringing into contact a hydrocarbon feedstock containing a $C_2$, $C_3$ and/or $C_4$ paraffinic hydrocarbon with a catalyst composition comprising an aluminosilicate in which the molar ratio of silica to alumina is at least 5:1 and loaded with a compound of (a) gallium and (b) at least one rare earth metal. Preferred feedstocks are those containing a $C_3$ and/or $C_4$ paraffinic hydrocarbon.

The aluminosilicates have a silica to alumina molar ratio above 5:1, suitably from 20:1 to 150:1 and are suitably MFI type zeolites of the general formula: $M_{2/n}O.Al_2O_3.ySiO_2.zH_2O$ wherein M is a cation of valence n, y is an integer greater than 5 and z is from 0 to 40. The cation, M, is preferably an alkali metal ion, an alkaline earth metal ion or a proton. MFI zeolites belong to a class of known zeolite structure types published by The Structure Commission of the International Zeolite Association ("Atlas of Zeolite Structure Types", by Meier, W.M. and Olsen, D.H. (1978), distributed by Polycrystal Book Service, Pittsburgh, Pa, USA). Specific examples of such zeolites are the ZSM varieties especially ZSM-5. These zeolites are usually produced from a silica source, an alumina source, an alkali metal hydroxide and a nitrogen-containing base such as ammonia or an alkanolamine, for example diethanolamine. Zeolites made in this manner are described in our published European Patent Application Nos. 002899 and 0002900.

The catalyst composition used in this invention comprises a zeolite loaded with a compound of gallium and a compound of a rare earth metal. The zeolite used is preferably an MFI type zeolite having a silicon to aluminium atomic ratio in the range of 10:1 to 30:1, preferably 12:1 to 20:1. The loading of the catalyst with gallium may be carried out as described in our prior published European Patent Application Nos. 0024930 or 0147111. Whichever method is used for gallium loading it is preferable that the gallium content of the gallium zeolite is from 0.5 to 2% w/w.

The gallium loaded zeolite is then steamed prior to being loaded with the rare earth metal compound which is preferably a lanthanum compound or a mixture of rare earths containing lanthanum such as misch metal. Misch metal is principally a mixture of lanthanum, cerium and praseodymium. Other suitable rare earth compounds include those of erbium, praseodymium, neodymium and cerium. The steaming of the gallium loaded zeolite is suitably carried out in two stages: an initial stage at around 550° C. for a duration of 1-5 hours using a gas stream containing at least 15% w/w of water vapour or steam which is cooled down thereafter to room temperature and reheated in steam using a gas stream containing a higher concentration of steam e.g. 20% w/w for a similar duration as previously stated but now being cooled down, e.g. in dry air, the total duration of the two stages combined being no more than 5-6 hours for a total gas hourly space velocity (GHSV,$hr^{-1}$), in the range of 200-5000, preferably from 800-3000, typically 1000-2000.

The loading of the rare earth metal compound is suitably carried out after the steam treatment of the gallium loaded zeolite. For instance, if the rare earth metal used is lanthanum, the gallium loaded zeolite preferably brought into contact with a solution of lanthanum nitrate. This step may be carried out at room temperature and the zeolite now loaded with both gallium and lanthanum can be dried slowly e.g. between 50°-100° C. over 3 days.

The catalyst composition preferably has up to 2%, especially up to 1% w/w, of rare earth metal, especially lanthanum. For example, the catalyst may contain from 0.2 to 1% w/w of gallium and from 0.1 to 2%, especially 0.1 to 0.8% w/w of rare earth, especially lanthanum.

The catalyst composition may be bound in a suitable binder such as for instance silica or alumina. It is preferable that the binder is free of phosphate ions. Whichever binder is used, the amount used should be such that it does not significantly alter the silicon to aluminium atomic ratio in the final bound composite with respect to the zeolite used. Typically, for a silica binder, the amount of binder used for instance should be 0.4 ($\pm10\%$) x mass of the zeolite used.

The hydrocarbon feedstock containing $C_2$, $C_3$ and/or $C_4$ paraffin hydrocarbons is converted to aromatic hydrocarbons or gasoline blending components.

The conversion by a gas phase process is suitably carried out at a temperature above 450° C., preferably from 475 to 650° C. Especially when the feedstock contains $C_3/C_4$ hydrocarbons, the reaction temperature is preferably less than 580° C., for example 475°-575° C.

Reaction pressures used are suitably from 1-20 bar absolute, preferably from 2-10 bar absolute.

The hydrocarbon feedstock is suitably brought into contact with the catalyst composition for a duration of 1-50 seconds, preferably from 5-20 seconds. The liquid hourly space velocity (LHSV,$hr^{-1}$) of the reactants is suitably from 0.5-8, preferably from 1-4.

If desired, ethane or other hydrocarbons may be added to $C_3/C_4$ feedstock components either from an external source or as a recycled product generated during the aromatisation of a $C_3/C_4$ feedstock. Such a mixed ethane containing feedstock of the gives results that are better than would be expected from combining the results obtained with the single feeds, and the addition of ethane has a beneficial effect that is not observed on diluting a $C_3/C_4$ feed with nitrogen (i.e. the effect is not simply caused by the reduction of partial pressures of reactants and products).

The process of the present invention is further illustrated with reference to the following Examples.

EXAMPLE 1

The Effect of Lanthanum Addition to the Usual Ga/MFI Catalyst

The preparation of the gallium loaded MFI zeolite catalysts is shown below; this was the reference catalyst Ga/MFI.

Reference Catalyst "CAT-2" Production Prior to Steaming

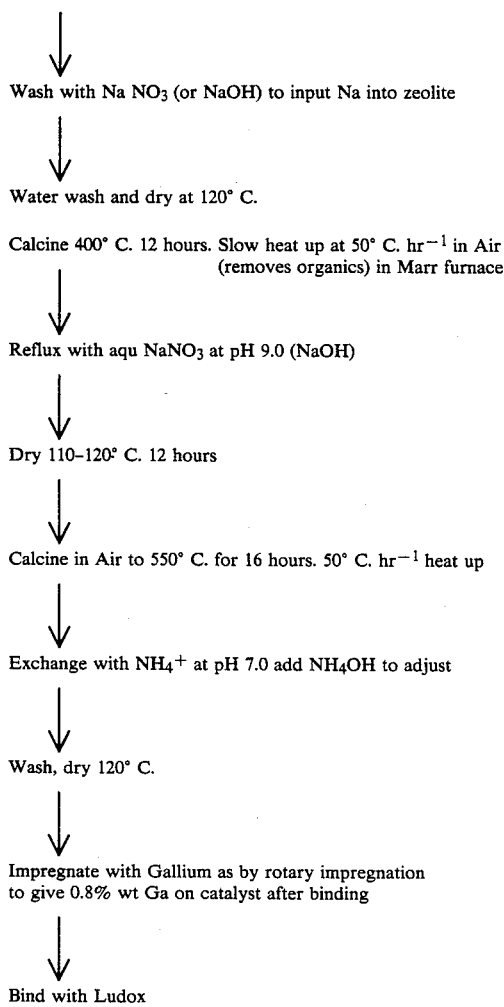

Raw Zeolite MFI - using diethanolamine as template

Wash with Na $NO_3$ (or NaOH) to input Na into zeolite

Water wash and dry at 120° C.

Calcine 400° C. 12 hours. Slow heat up at 50° C. $hr^{-1}$ in Air (removes organics) in Marr furnace Reflux with aqu $NaNO_3$ at pH 9.0 (NaOH)

Dry 110–120° C. 12 hours

Calcine in Air to 550° C. for 16 hours. 50° C. $hr^{-1}$ heat up

Exchange with $NH_4^+$ at pH 7.0 add $NH_4OH$ to adjust

Wash, dry 120° C.

Impregnate with Gallium as by rotary impregnation to give 0.8% wt Ga on catalyst after binding Bind with Ludox After binding with Ludox, Ga/MFI catalyst was steamed under the following steaming conditions, that is: T=550° C., $H_2O$=20% v/v for 2 hours to provide the catalyst "Cat-2".

An aliquot of the same bound catalyst was then steamed in two stages:

(a) T=550° C., $H_2O$=15% v/v for 2 hours, then allowed to cool down to room temperature.

(b) T=545° C., $H_2O$=20% v/v for 2 hours, then allowed to cool down under dry air. In both cases total GHSV was 2000.

Lanthanum was added after the second steaming stage (b), at room temperature, in the form of a La nitrate solution. The catalyst was then dried in an oven at 70° C. for three days to form the catalyst "Cat-1" used in the present invention. "Cat-1" and "Cat-2" were then progressively heated up to 540° C. under nitrogen and finally hydrogen-treated at 540=C for 1 hour before testing for catalytic activity.

Metal Contents

Cat-1 (La+Ga) : Ga 0.8% wt+La 0.6% wt

Cat-2 (Ga) : Ga 0.8% wt

Catalytic Testing

Both catalysts were studied using a 20 cc pilot plate under the following conditions (WHSV=weight hourly space velocity, $hr^{-1}$): Cat-1: P=3 bars,T=544° C.,LHSV=1.13,WHSV=0.87,Feed=Propane (SP5 grade) Cat-2: P=3 bars,T=549° C.,LHSV=1.03,WHSV=0.79,Feed=Propane (SP5 grade)

This Ga/MFI catalyst "Cat-2" was run for 100 hours on stream (HOS), and test periods were carried out at HOS=4.5,27,51,74; the La+Ga catalyst was run for 127 hours on stream, with a run interruption between the third and fourth test period (at this stage the catalyst was cooled down under nitrogen, then reheated under nitrogen and restarted using propane feed). Test periods were carried out at HOS=4.5,27,51,81,106 for this catalyst.

Results and Comments

The results are shown in Talbe 1. They very clearly show a strong improvement in selectivity for the Lanthanum +Gallium catalyst "Cat-1" as compared with the reference catalyst "Cat-2"; the average selectivity for Cat 1 is 59.6, against 49.6 for Cat-2. Selectivity is defined as % w relative to products heavier than $C_4$s. Conversion is defined as $C_3+C_4$ conversion % w.

The compared variations of conversion values versus time strongly suggest that Cat-1 is more stable than Cat-2, although it has been submitted to a second start (with a higher WHSV for 3 hours). In absolute values, the conversion level of Cat-1 becomes higher than that of Cat-2 after 80 HOS, though it is slightly lower for the first three runs as is usually observed for oversteamed catalysts. It must be stressed that a typical reference catalyst such as Cat-2, if oversteamed, normally shows a higher stability but poorer conversion and similar selectivity. For instance, an oversteamed catalyst Cat-2 tested under the same conditions, using the same pilot plant for 100 HOS, gave a 60% conversion and about 50–52% selectivity. In the case of Cat-1 and Cat-2 studied in this work, the conversion level was much higher (95 - 87% over 85 HOS for Cat-1, 96 to 82% for Cat-2), and the initial drop in conversion for the oversteamed La-Ga catalyst is almost negligible.

TABLE 1

| HOS | Conversion Cat 1 | Selectivity to aromatics Cat 1 | Conversion Cat 2 | Selectivity to aromatics Cat 2 |
|---|---|---|---|---|
| 4.5 | 94.54 | 59.67 | 96.24 | 48.61 |
| 27.0 | 92.72 | 59.69 | 94.33 | 48.55 |

TABLE 1-continued

| HOS | Conversion Cat 1 | Selectivity to aromatics Cat 1 | Conversion Cat 2 | Selectivity to aromatics Cat 2 |
|---|---|---|---|---|
| 51.0 | 88.52 | 59.51 | 89.14 | 50.24 |
| 74.0 | | | 82.29 | 51.08 |
| 81.0 | 86.62 | 58.81 | | |
| 106.0 | 78.28 | 60.07 | | |

EXAMPLE 2

250g ZSM-5 zeolite, silica to alumina ratio 36:1, prepared by the method described in EP-A-30811, was washed with 180ml of 70% nitric acid in 1070 ml of distilled water by stirring for 30 minutes. The zeolite was filtered and washed with 4×500ml portions of distilled water, dried under vacuum at 100° C. overnight, and then sieved to less than 500 microns. The sieved zeolite was calcined in a steel tray at 550° C. for 60 hours under a flow of air of 2.5l/min.

The calcined zeolite was refluxed for 4 hours in a solution of 250 ml gallium nitrate (0.025g of Ga per ml) and 1750 ml of distilled water, the solution being buffered to pH 2.3 with ammonia solution. The zeolite was filtered hot and washed with 4 x 500 ml portions of distilled water then dried in a vacuum oven at 100° C. overnight.

The dried zeolite was sieved to less than 500 microns and mixed with a silica binder (LUDOX AS40, Trade Mark) to give a dry zeolite to binder ratio of 60:40. The bound zeolite was sieved to give a particle size of 8-30 mesh, and this material was treated with 16% v/v steam in air at 550° C. for 2 hours at a gas hourly space velocity of 200h$^{-1}$. The resultant catalyst contained 0.3% wt gallium.

20 ml portions (14g) of this product were mixed with 15 ml of distilled water to which solutions of various lanthanide salts had been added. The catalyst was dried in a vacuum at 100° C. overnight.

20 ml (14g) portions of the resultant catalysts were placed in stainless steel tubular reactors and temperatures were raised to 535° C. under flowing hydrogen at atmospheric pressure. When the reactor had come to temperature the hydrogen flow was stopped and the reactor purged with nitrogen. The pressure was raised to 2 bar absolute and propane was passed through the reactor at a rate of 0.7 weight hourly space velocity, the furnace controls being adjusted to maintain an average bed temperature of 535° C. The reaction products were separated into gas and liquid phases in a condensor system and analysed by gas chromatography. After the reaction, the catalysts were examined for carbon deposits.

The results of the experiment are given in Table 2.

TABLE 2

| Catalyst Tested | HOS | Selectivity to Aromatics | wt % C deposited on catalyst |
|---|---|---|---|
| MFI/Ga 0.3% wt | 4 | 49.06 | |
| | 23 | 51.34 | 1.6 |
| MFI/Ga 0.3% wt/ | 4 | 49.94 | |
| Pr 1% wt | 23 | 52.66 | 1.1 |
| MFI/Ga 0.3% wt/ | 4 | 49.45 | |
| Er 0.97% wt | 23 | 52.66 | 1.3 |
| MFI/Ga 0.3% wt/ | 4 | 50.59 | |
| Nd 0.99% wt | 23 | 52.29 | 1.0 |
| MFI/Ga 0.3% wt/ | 4 | 51.83 | |
| Ce 1% wt | 23 | 53.47 | 1.1 |

EXAMPLE 3

Catalysts were prepared as described above comprising MFI/0.7wt%Ga and MFI/0.7% wtGa/1%wtLa. These catalysts were then tested as described above under the following conditions: feedstock: ethane; catalyst charge: 6g; temperature: 60° C.; pressure:6 bar; WHSV:1.0

The results are given in Table 3.

TABLE 3

| Catalyst Tested | HOS | Selectivity to Aromatics | wt % C deposited on catalyst |
|---|---|---|---|
| MFI/Ga 0.7% wt | 3 | 52.0 | |
| | 24 | 53.9 | 5.0 |
| MFI/Ga 0.7% wt/ | 3 | 53.9 | |
| La 1% wt | 24 | 56.2 | 3.4 |

I claim:

1. A process for producing aromatic hydrocarbons comprising bringing into contact a hydrocarbon feedstock containing a $C_2$, $C_3$ and/or $C_4$ paraffinic hydrocarbon with a catalyst composition comprising an aluminosilicate in which the molar ratio of silica to alumina is at least 5:1 and loaded with a compound of (a) gallium and (b) at least one rare earth metal.

2. A process as claimed in claim 1 in which the aluminosilicate is an MFI type zeolite of the general formula $$M_{2/n}O \cdot Al_2O_3 \cdot ySiO_2 \cdot zH_2O$$

wherein M is a cation of value n, y is an integer greater than 5, and z is from 0 to 40.

3. A process as claimed in claim 1, in which the catalyst composition contains 0.2 to 1% w/w of gallium and from 0.1 to 2% w/w of rare earth metal.

4. A process as claimed in claim 1, in which the catalyst composition contains lanthanum, erbium, praseodymium, neodymium and/or cerium.

5. A process as claimed in claim 1, in which the catalyst composition contains lanthanum.

6. A process as claimed in claim 1, in which the temperature is in the range of from 475° to 650° C.

7. A process as claimed in claim 20 in which the feedstock contains a $C_3$ and/or $C_4$ paraffinic hydrocarbon and the temperature is less than 580° C.

8. A process as claimed in claim 2 in which the catalyst composition contains 0.2 to 1% w/w of gallium and from 0.1 to 2% w/w of rare earth metal.

9. A process as claimed in claim 2 in which the catalyst composition contains lanthanum, erbium, praseodymium, neodymium and/or cerium.

10. A process as claimed in claim 3 in which the catalyst composition contains lanthanum, erbium, praseodymium, neodymium and/or cerium.

11. A process as claimed in claim 2 in which the catalyst composition contains lanthanum.

12. A process as claimed in claim 3 in which the catalyst composition contains lanthanum.

* * * * *